(12) United States Patent
Gylleby

(10) Patent No.: US 10,576,213 B2
(45) Date of Patent: Mar. 3, 2020

(54) AUTOINJECTOR WITH DELAYED SIGNAL OF COMPLETE MEDICATION DELIVERY

(71) Applicant: Carebay Europe Ltd., Sliema (MT)

(72) Inventor: Stefan Gylleby, Stockholm (SE)

(73) Assignee: SHL MEDICAL AG, Zug (CH)

( * ) Notice: Subject to any disclaimer, the term of this patent is extended or adjusted under 35 U.S.C. 154(b) by 250 days.

(21) Appl. No.: 15/519,798

(22) PCT Filed: Oct. 28, 2015

(86) PCT No.: PCT/EP2015/074966
§ 371 (c)(1),
(2) Date: Apr. 17, 2017

(87) PCT Pub. No.: WO2016/071174
PCT Pub. Date: May 12, 2016

(65) Prior Publication Data
US 2017/0239421 A1 Aug. 24, 2017

(30) Foreign Application Priority Data

Nov. 4, 2014 (SE) .................................... 1451317

(51) Int. Cl.
*A61M 5/315* (2006.01)
*A61M 5/20* (2006.01)
(Continued)

(52) U.S. Cl.
CPC ........ *A61M 5/3157* (2013.01); *A61M 5/2033* (2013.01); *A61M 5/24* (2013.01);
(Continued)

(58) Field of Classification Search
CPC .............. A61M 5/2033; A61M 5/3157; A61M 2005/2013; A61M 2005/206;
(Continued)

(56) References Cited

U.S. PATENT DOCUMENTS 6,620,133 B1 * 9/2003 Steck ...................... A61M 5/20
604/131
2014/0243751 A1 * 8/2014 Brereton ............. A61M 5/2033
604/197
(Continued)

FOREIGN PATENT DOCUMENTS

WO 2011043714 A1 4/2011
WO 2012022810 A2 2/2012
(Continued)

*Primary Examiner* — Kami A Bosworth
(74) *Attorney, Agent, or Firm* — McDonnell Boehnen Hulbert & Berghoff LLP

(57) ABSTRACT

The present invention relates to a medicament delivery device comprising: a housing; a drive mechanism arranged to act on a plunger rod; a release mechanism interactively connected to the drive mechanism for releasing the drive mechanism from a pre-tensioned state; and a signal generating mechanism for generating an audible and/or tactile and/or visual signal indicating that a medicament has been completely delivered. The signal generating mechanism is operably connected to said drive mechanism such that it is arranged movable in a longitudinal direction in relation to said drive mechanism. Said drive mechanism is arranged with a signal release mechanism capable of activating said signal generating mechanism at a certain longitudinal position of said drive mechanism after its release, for generating an audible and/or tactile and/or visual signal. Said signal generating mechanism comprises a signal delay mechanism.

21 Claims, 14 Drawing Sheets

(51) Int. Cl.
*A61M 5/32* (2006.01)
*A61M 5/46* (2006.01)
*A61M 5/24* (2006.01)
*A61M 5/31* (2006.01)

(52) U.S. Cl.
CPC .......... *A61M 5/326* (2013.01); *A61M 5/3245* (2013.01); *A61M 5/46* (2013.01); *A61M 2005/202* (2013.01); *A61M 2005/206* (2013.01); *A61M 2005/208* (2013.01); *A61M 2005/2407* (2013.01); *A61M 2005/2488* (2013.01); *A61M 2005/3143* (2013.01); *A61M 2005/3247* (2013.01); *A61M 2205/581* (2013.01); *A61M 2205/582* (2013.01); *A61M 2205/583* (2013.01)

(58) Field of Classification Search
CPC .... A61M 2005/208; A61M 2005/3143; A61M 2005/3267; A61M 2205/43; A61M 2205/581; A61M 2205/582; A61M 2205/583
See application file for complete search history.

(56) References Cited

U.S. PATENT DOCUMENTS

| | | | |
|---|---|---|---|
| 2014/0324023 A1* | 10/2014 | Krijger | A61M 5/20 604/506 |
| 2015/0119814 A1 | 4/2015 | Fabien et al. | |
| 2015/0202368 A1* | 7/2015 | Carrel | A61M 5/2033 604/136 |
| 2016/0008541 A1* | 1/2016 | Hirschel | A61M 5/2033 604/506 |
| 2016/0129187 A1* | 5/2016 | Roervig | A61M 5/3155 604/207 |
| 2016/0193415 A1* | 7/2016 | Cowe | A61M 5/2033 604/228 |
| 2017/0007765 A1* | 1/2017 | Cowe | A61M 5/172 |

FOREIGN PATENT DOCUMENTS

| | | |
|---|---|---|
| WO | 2012117255 A1 | 9/2012 |
| WO | 2013175139 A1 | 11/2013 |
| WO | 2013178512 A1 | 12/2013 |
| WO | 2014029621 A1 | 2/2014 |
| WO | 2015185311 A1 | 12/2015 |

* cited by examiner

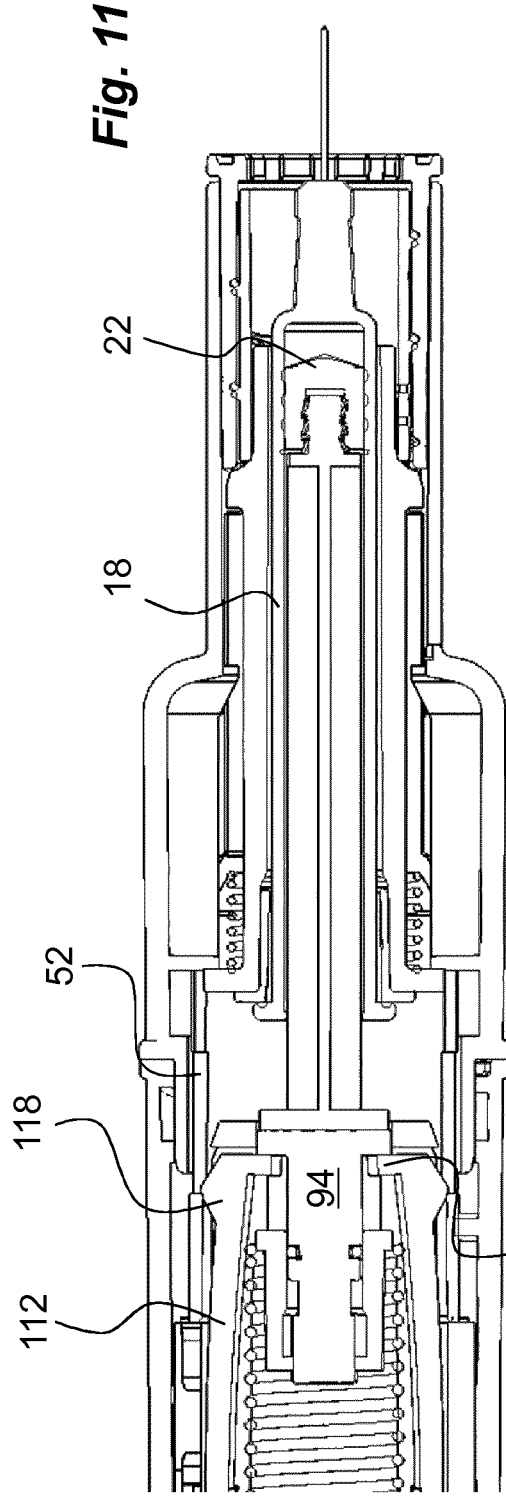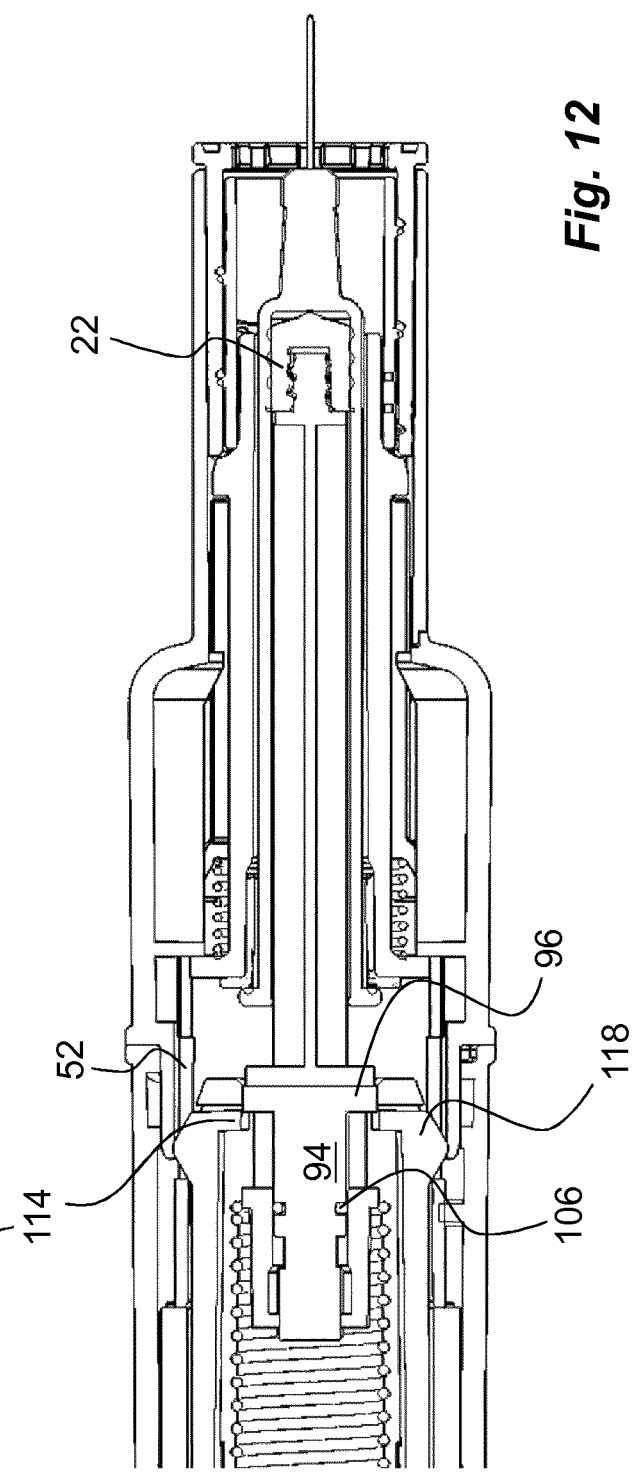

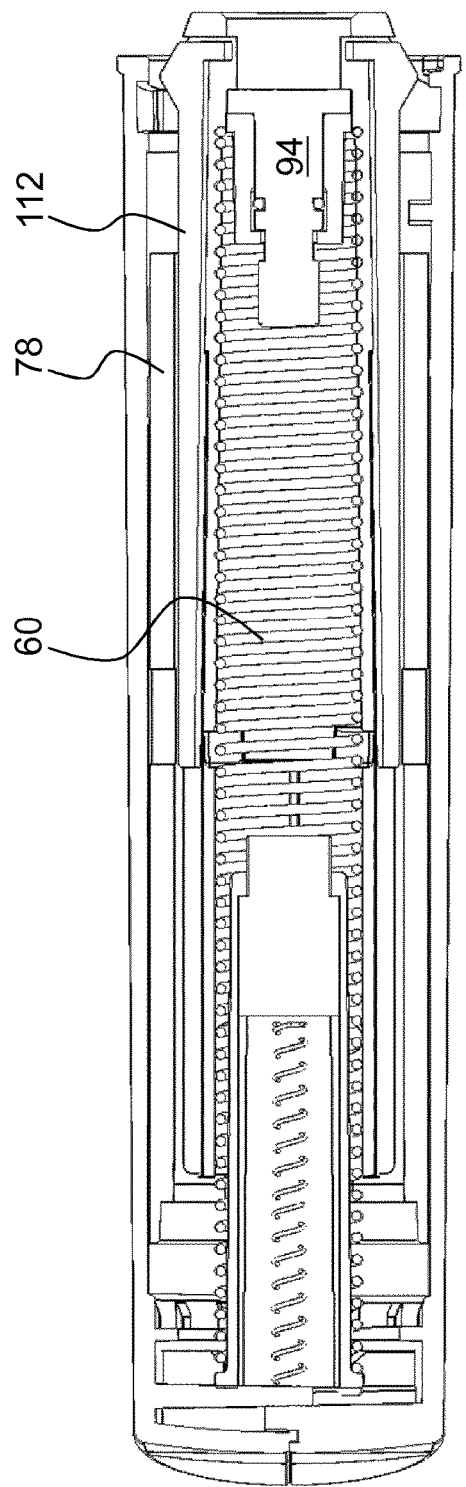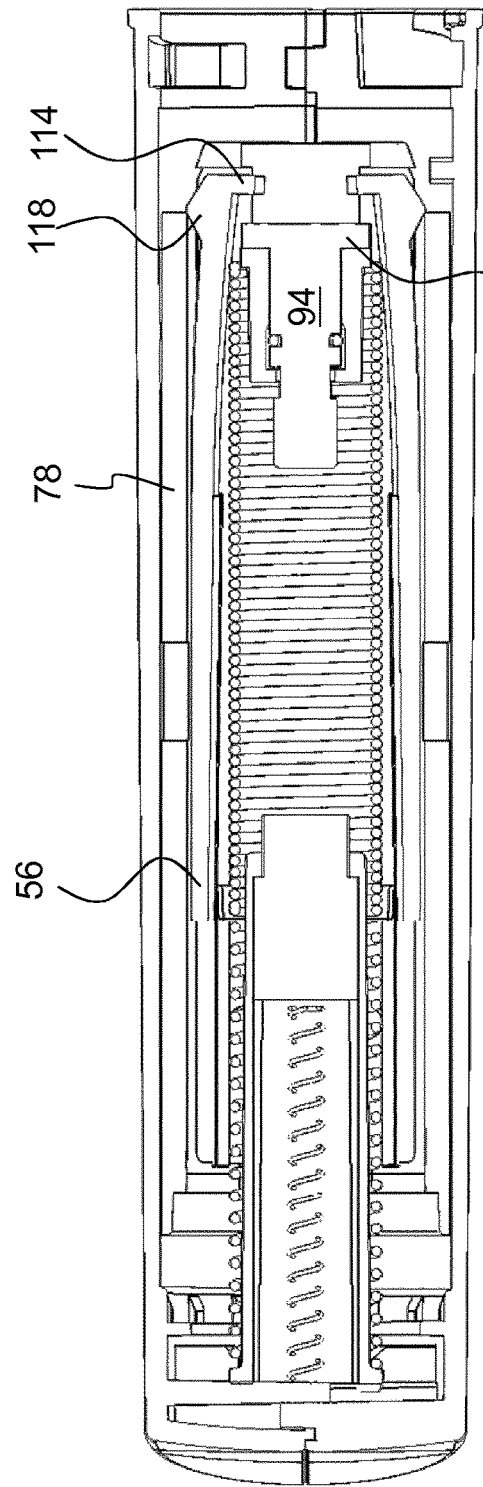

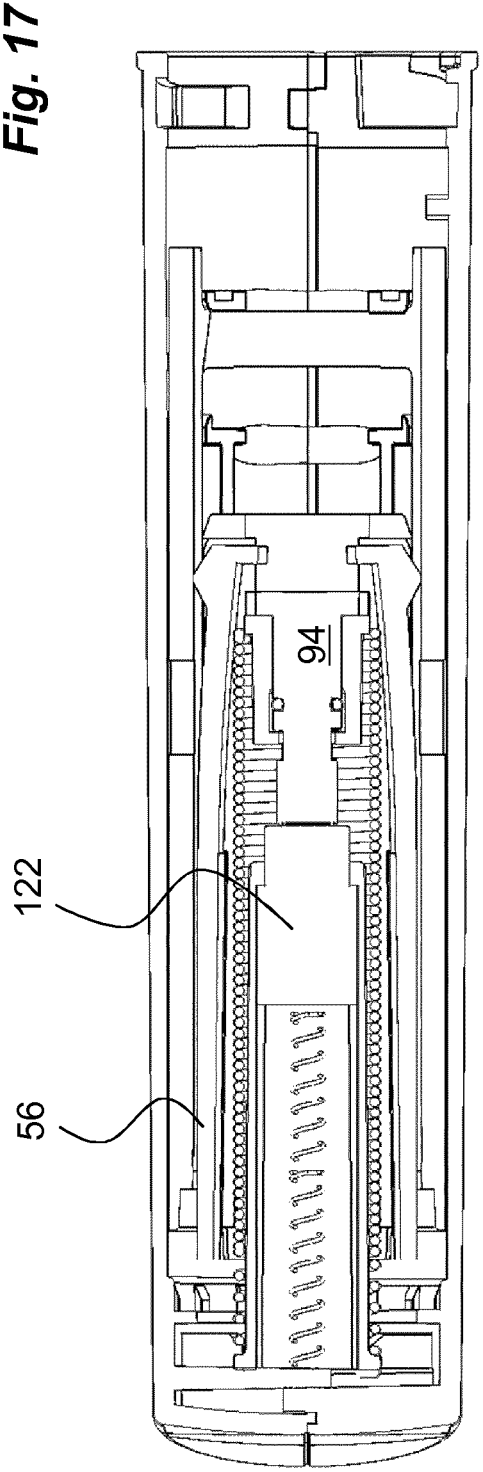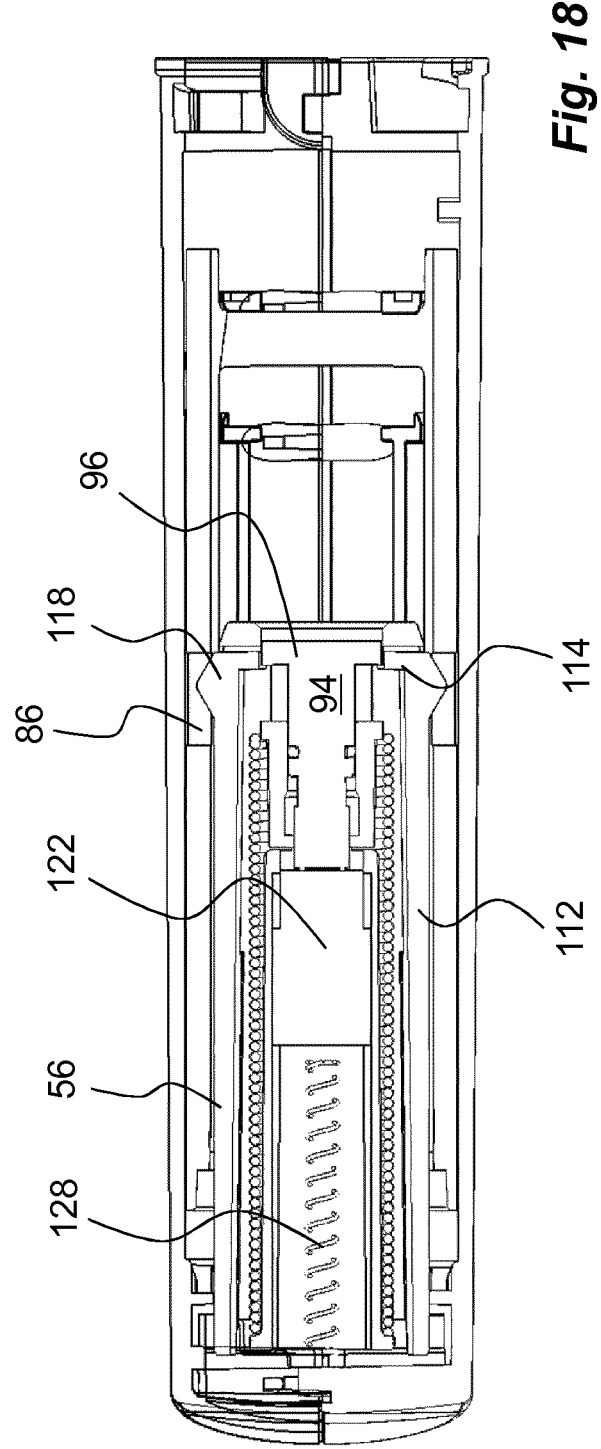

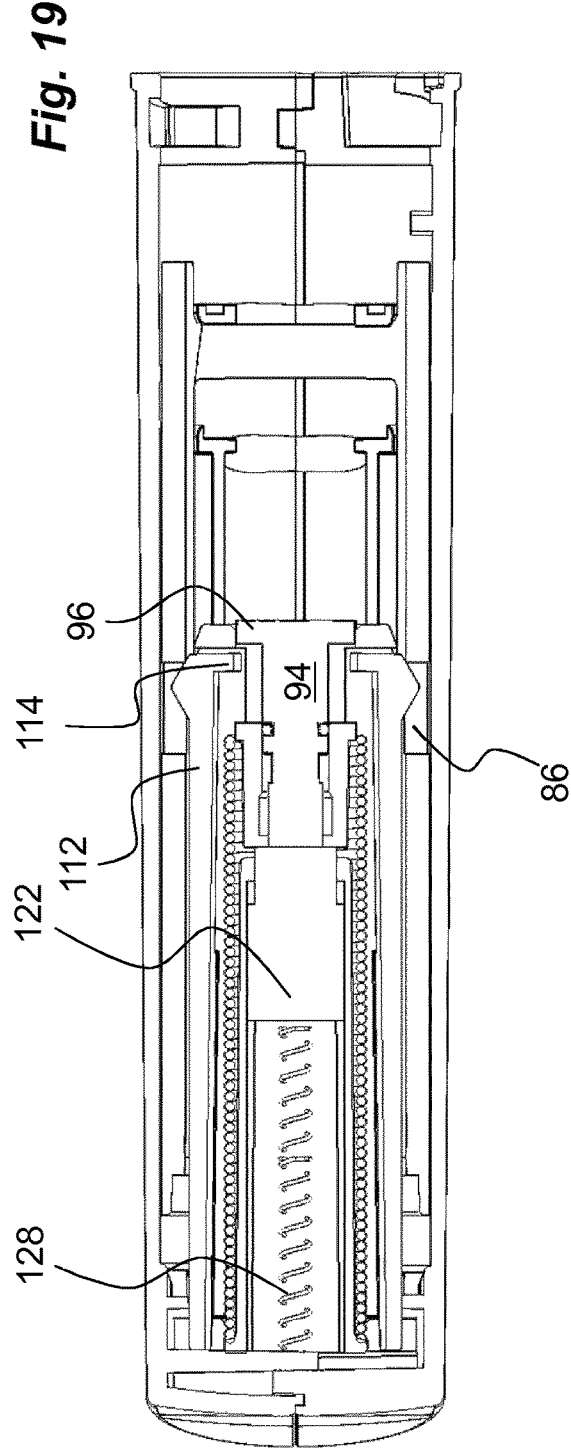
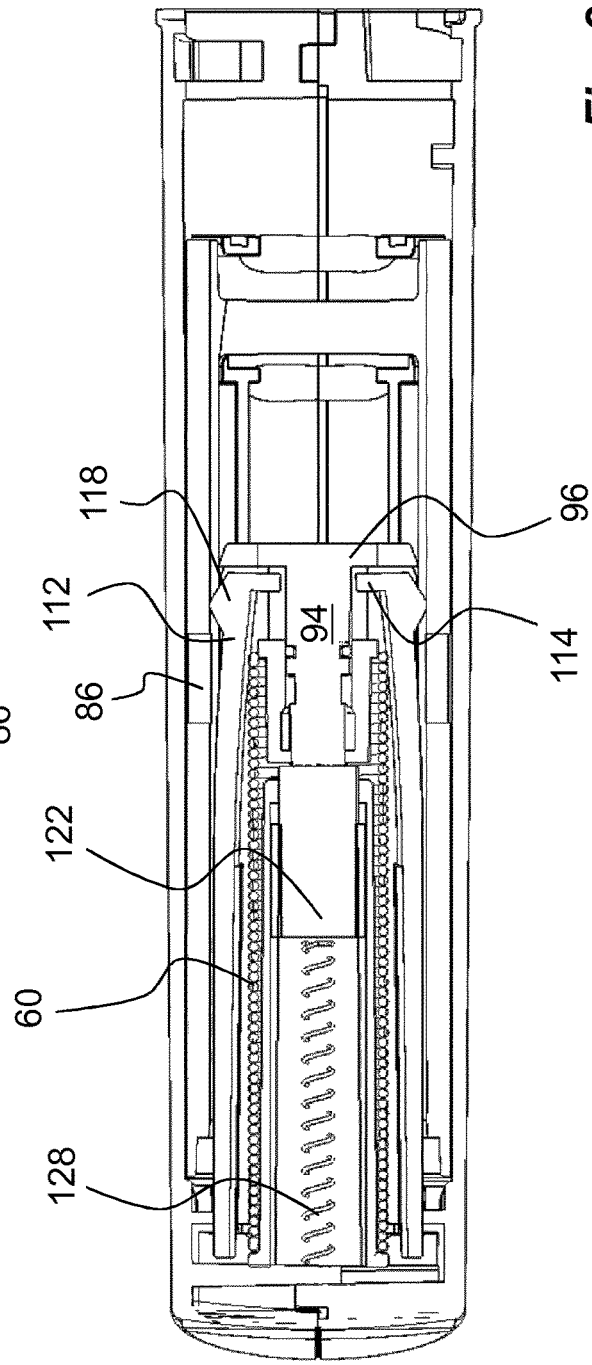

AUTOINJECTOR WITH DELAYED SIGNAL OF COMPLETE MEDICATION DELIVERY

CROSS REFERENCE TO RELATED APPLICATIONS

The present application is a U.S. National Phase Application pursuant to 35 U.S.C. § 371 of International Application No. PCT/EP2015/074966 filed Oct. 28, 2015, which claims priority to Swedish Patent Application No. 1451317-0 filed Nov. 4, 2014. The entire disclosure contents of these applications are herewith incorporated by reference into the present application.

TECHNICAL AREA

The present invention relates to a medicament delivery device and in particular to a device capable of indicating to a user when a medicament delivery sequence has been completed such that it is safe to remove the device from the dose delivery site.

BACKGROUND OF INVENTION

Many medicament delivery devices are developed for self-administration, i.e. a user performs the medicament delivery her-, or himself. This requires a medicament delivery device, which is reliable, accurate, safe and easy to use. In order to meet these requirements, the risk of human errors must be minimized, the number of actions needed to be performed in order to receive a dose need to be reduced and the device must be intuitive to use. Thus, in order to minimize the risk of human errors, it is desirable to have a device that accurately provides a user with confirmation that he/she has received a complete dose of medicament.

Medicament delivery devices such as injection devices providing automatic or manual delivery member insertion, automatic injection of a medicament, automatic delivery member retraction or automatic covering of the delivery member are known in the art. Though these injection devices provide many benefits, there is always room for improvement. For example, a device that provides both a complete delivery of medicament and release of a member that produces a reliable audible and/or tactile and/or visible confirmation to the user that the delivery has been completed has hitherto required extremely tight tolerances during manufacturing.

For example, release of a member that produces a reliable audible and/or tactile and/or visible confirmation to the user that the delivery has been completed is disclosed in WO2011043714A1. The release is accomplished by disengaging a plunger rod from a second activator member once the plunger rod has terminated its displacement for delivering the medicament. The termination of the plunger rod displacement and the disengaging of the plunger rod from the second activator member must occur simultaneously if both a complete delivery of a medicament and a release of the second activator member which produces the reliable audible and/or tactile and/or visible confirmation to the user that the delivery has been completed are to be accomplished.

Thus, in WO2011043714A1 there is only one mechanical position that is used to activate the release of the second activation member at the point where it is expected that the plunger displacement will terminate. The precision of the timing of the termination of plunger displacement and disengagement of the plunger from the second activation member relies on the manufacturing and assembly dimensions of the parts of the device and thus the tolerances play an important role in the proper functioning of the device.

Thus, in order to compensate for component tolerances a signal generating member needs to be released before the plunger displacement has terminated. A user may then be prone to remove the device from the delivery site, accidentally causing interruption of the medicament delivery. In order to ensure a complete and accurate delivery of a medicament, all the parts or components of the device must be manufactured to very tight tolerances, leading to high manufacturing and assembling costs.

Thus, it would be an improvement in the art to provide a medicament delivery device that can be manufactured and assembled, having reliable functions, such as a complete delivery of a medicament followed by an audible and/or tactile and/or visible confirmation to the user that the delivery has been completed.

BRIEF DESCRIPTION OF INVENTION

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The aim of the present invention is to remedy the drawbacks of the state of the art medicament delivery devices. This aim is obtained by a medicament delivery device comprising the features of the independent patent claim 1. Preferable embodiments of the invention form the subject of the dependent patent claims.

According to the present invention, it comprises a medicament delivery device provided with a preferably elongated housing that has a distal end and a proximal end. The housing may be adapted to receive a medicament container with a delivery member. The delivery member may either be attached to the medicament container or be made integral with it. The delivery member may alternatively be removably connectable to the medicament container. The connection elements may be of different type, like threads, bayonet connections or luer connections, for example.

The medicament delivery device may further preferably comprise a drive mechanism arranged to act on a plunger rod, where the plunger rod is arranged to act on the medicament container for providing automatic delivery of the medicament. The drive mechanism is preferably pre-tensioned and will preferably interact with a release mechanism. The drive mechanism may on the one hand be automatically operated such that a pressing of the device against a dose delivery site will activate the drive mechanism. On the other hand, the drive mechanism may be manually operated such that the user activates the drive mechanism by e.g. pressing a button or the like.

According to a preferable solution, the medicament delivery device may comprise a signal generating mechanism for generating an audible and/or tactile and/or visual signal indicating that the medicament has been completely delivered. The signal generating mechanism is preferably operably connected to the drive mechanism such that it is arranged movable in a longitudinal direction in relation to said drive mechanism. The movement in the longitudinal direction facilitates the design and generation of a signal in that very few components or special features are necessary.

In order to activate the signal generating mechanism, the drive mechanism may preferably be arranged with a release mechanism capable of activating said signal generating mechanism at a certain longitudinal position of said drive mechanism after its release, for generating an audible and/or tactile and/or visual signal. Thus, the signal generating mechanism is activated by the release mechanism at a certain position. This position may be chosen depending on the desired function and desired indication time. In a favourable scenario, the signal may be generated after completed injection sequence so that the user is sure that it is safe to remove the device from the delivery site.

In order to ascertain that the signal is generated after the injection sequence has ended, the signal generating mechanism may comprise a delay mechanism operably arranged to delay the generation of the signal after activation of said signal generating mechanism. The delay mechanism can be configured to vary the delay time depending on the desired end function.

According to a favourable solution, the signal generating mechanism may comprise a signal generating element, where the delay mechanism may comprise a friction enhancing element operably connected to said signal generating element and arranged to act between said signal generating element and said drive mechanism. With such a solution, friction is used to delay the signal by slowing the movement of the signal generating element.

According to one possible solution, the signal generating element may be arranged with a generally tubular body, arranged slidable in a correspondingly shaped passage, and wherein said friction enhancing element is arranged to act between the body and the passage. This may provide a functional and yet simple design where the friction enhancing element is slowing down the movement of the tubular body relative to the passage.

The passage may have a first section as seen in a longitudinal direction having a diameter such that said friction enhancing element is in contact with the first section, and a second section having a diameter such that the friction enhancing element is not in contact with the second section. Thus the first section sets the length or time the signalling is delayed due to the friction. Then, when the friction enhancing element reaches the second section, the signal generating element is free to move relative the drive mechanism, thereby providing a signal.

According one aspect of the invention for generating a signal, the signal generating element may be arranged with an abutment surface, operably arranged to interact with a corresponding abutment surface on the plunger rod driver for creating an audible and/or tactile signal when the abutment surfaces are moved in contact with each other. Thus when the second section is reached, the signal element is accelerated until the abutment surfaces hit each other, creating the signal. In that respect, the abutment surfaces may be positioned with a distance between each other when said friction enhancing element is moved from said first section to said second section.

Further, the signal generating mechanism may comprise radially flexible arms, such that the arms may flex between a holding position and a release position, and wherein the arms are held in a holding position by a radially outwardly positioned support surface, which support surface terminates at said certain longitudinal position of said drive mechanism. In this way, when the arms reach the end of the support surface, the signal generating element is released. This gives a positive and reliable function of the activation. In this respect, the termination of the support surface may be varied in relation to the position of the plunger rod driver, and thus the signal generating mechanism, providing possibilities to vary the activation point in relation to the injection sequence position.

If the device is intended to be used multiple times, it must be reset and a new medicament container supplied. Thus, also the signal generating mechanism must be reset. The device may therefore also comprise a signal element return mechanism operably connected to the signal generating mechanism for returning the signal element to its initial position when the drive mechanism is returned to its initial position.

According to an embodiment, the signal element return mechanism may comprise a return element capable of contacting said signal element causing a relative movement between the signal generating element and the drive mechanism. Thus, when the drive mechanism and the signal generating element are moved in the distal direction back to their initial position, the return element will stop the signal generating element causing a relative movement when the drive mechanism continues in the distal direction.

Further, the support surface may be arranged such as to act on said arms for holding said signal generating element after it has been brought to the initial position by said signal element return mechanism. Thus, the arms are again forced generally radially inwards, thereby locking the signal generating element to the drive mechanism.

According to a favourable solution, the friction enhancing element may be made of a resilient material. Suitable materials are rubber or plastic, but it is to be understood that other suitable materials may be used.

According to one solution, the friction enhancing element may be an O-ring. The signal generating element may then be arranged with a groove in which said O-ring may fit. The use of an O-ring provides a simple, yet reliable friction enhancing element of low cost.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
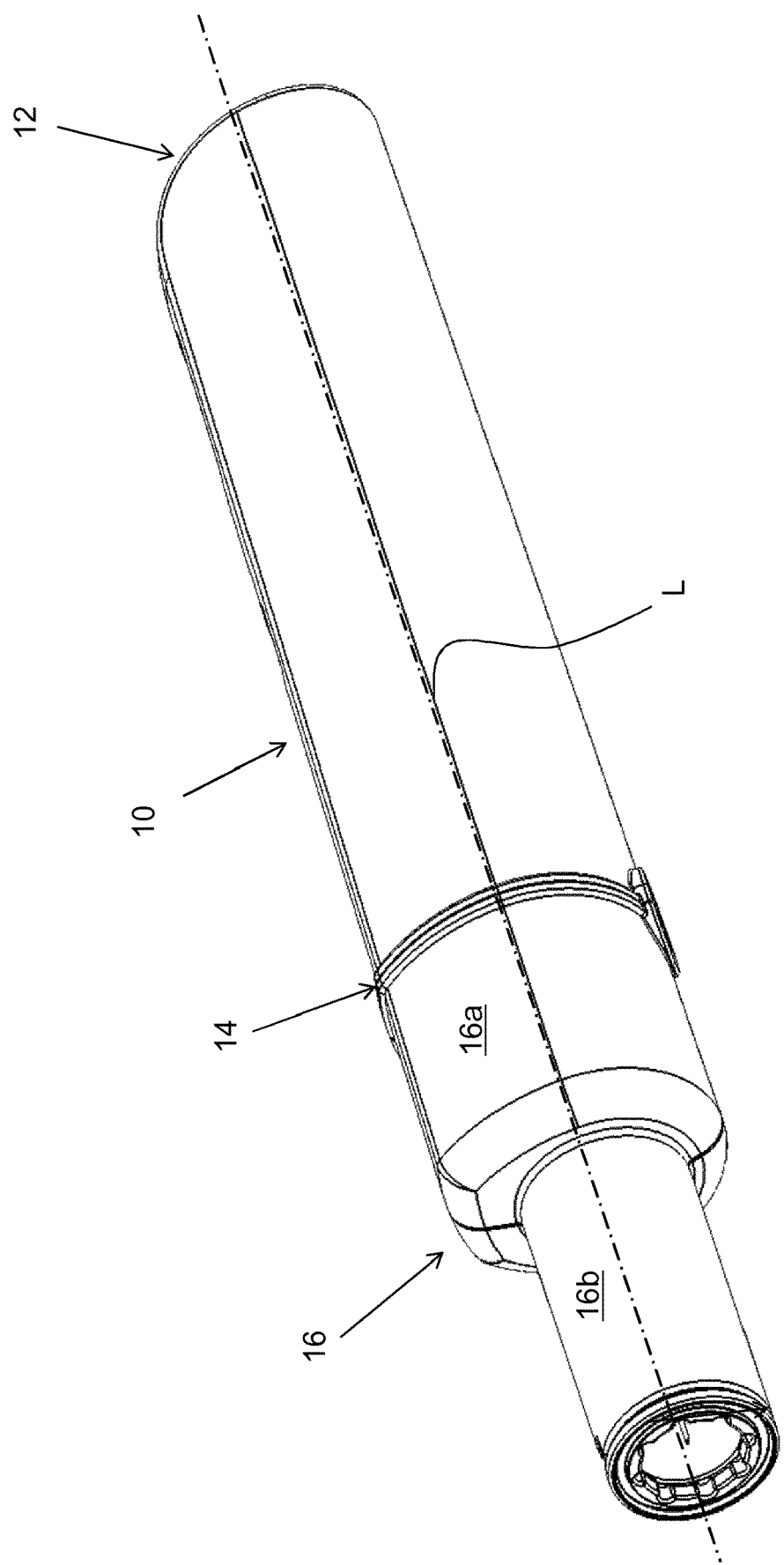
FIG. 1 shows a perspective view of a non-limiting embodiment of a medicament delivery device.
Figure 2:
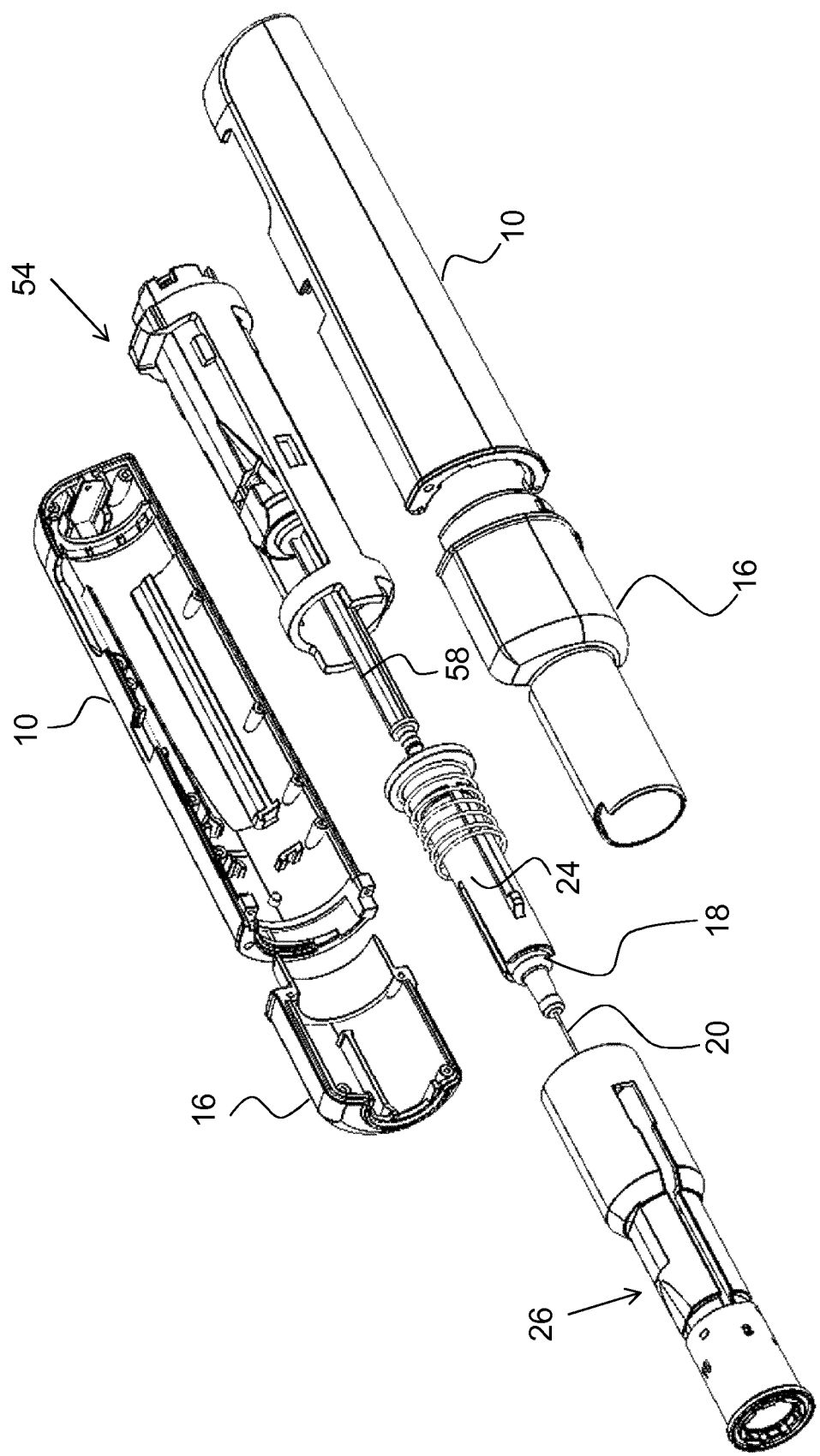
FIG. 2 is an exploded view of the embodiment of FIG. 1, FIGS. 3-9 are detailed views of components comprised in the embodiment of FIG. 1, and FIGS. 10-20 are detailed cross-sectional views of the embodiment of FIG. 1, showing different functional states.

The embodiment shown in the drawings comprises a generally elongated main housing 10 having a distal end 12 and a proximal end 14, FIG. 1. At the proximal end 14 a proximal housing part 16 is arranged to be releasably attached to the main housing 10 with a first tubular part 16*a*, FIGS. 1 and 2, having generally the same diameter as the main housing 10. Attaching elements could comprise threads, bayonet connections, snap-in elements and the like. In the embodiment shown the attaching elements are bayonet connections, as will be described below. The first tubular part 16a is arranged to a second tubular part 16b having a lesser diameter than the first tubular part 16a. As seen in the embodiment of FIG. 2, the proximal housing part 16 is arranged in two halves. It is to be understood that other designs are feasible for the desired function and/or due to production aspects.

Figure 3:
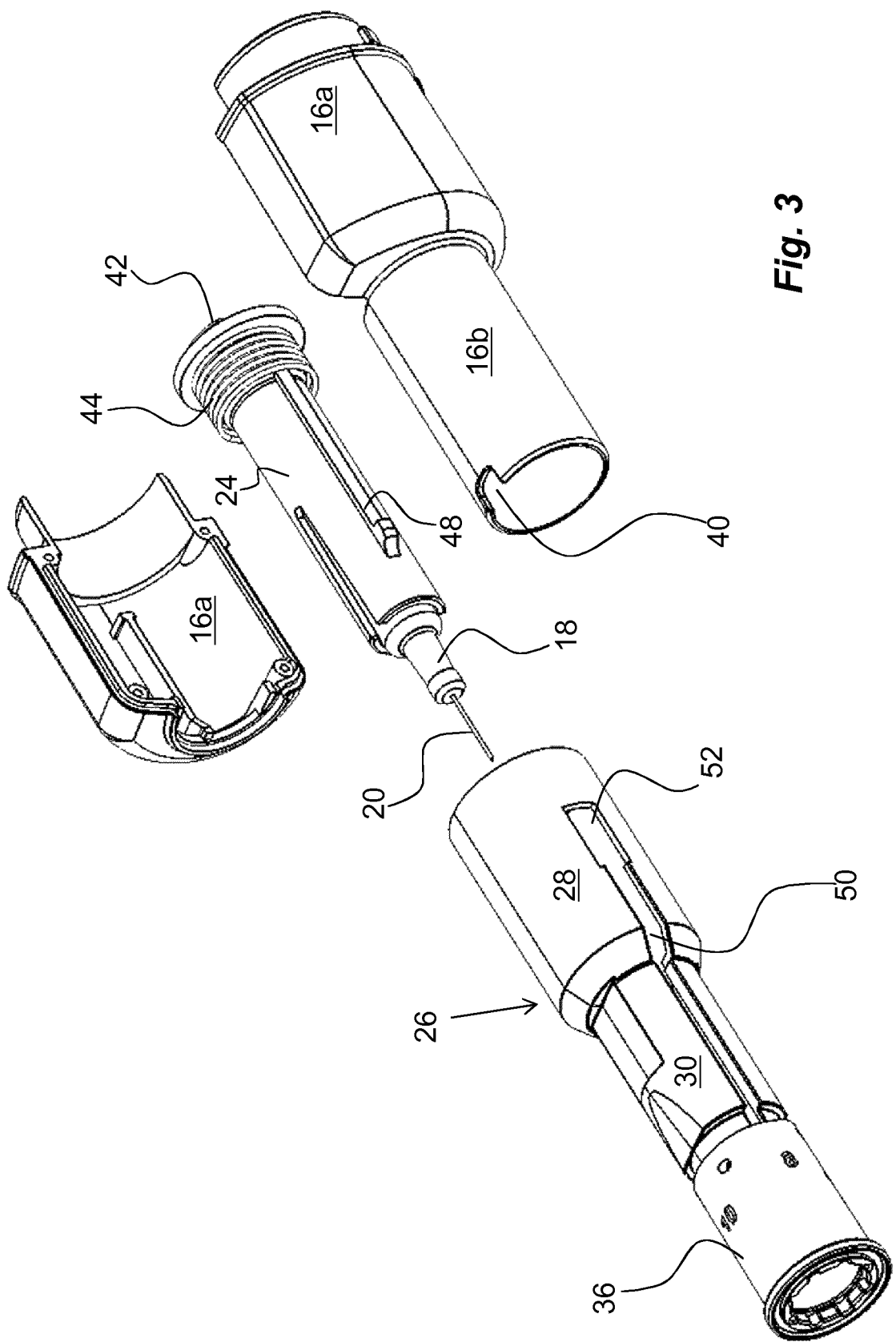

The proximal housing part 16 is designed to accommodate a medicament container 18, FIGS. 2 and 3. An appropriate medicament delivery member 20, FIGS. 2 and 3, is attached to, or made integral with, the medicament container 18. A movable stopper 22 is further arranged inside the medicament container, FIG. 11. The medicament container 18 is preferably arranged in a medicament container holder 24, FIGS. 2 and 3. The medicament container holder 24 is arranged to be slidable in the longitudinal direction as will be explained below.

Figure 4:
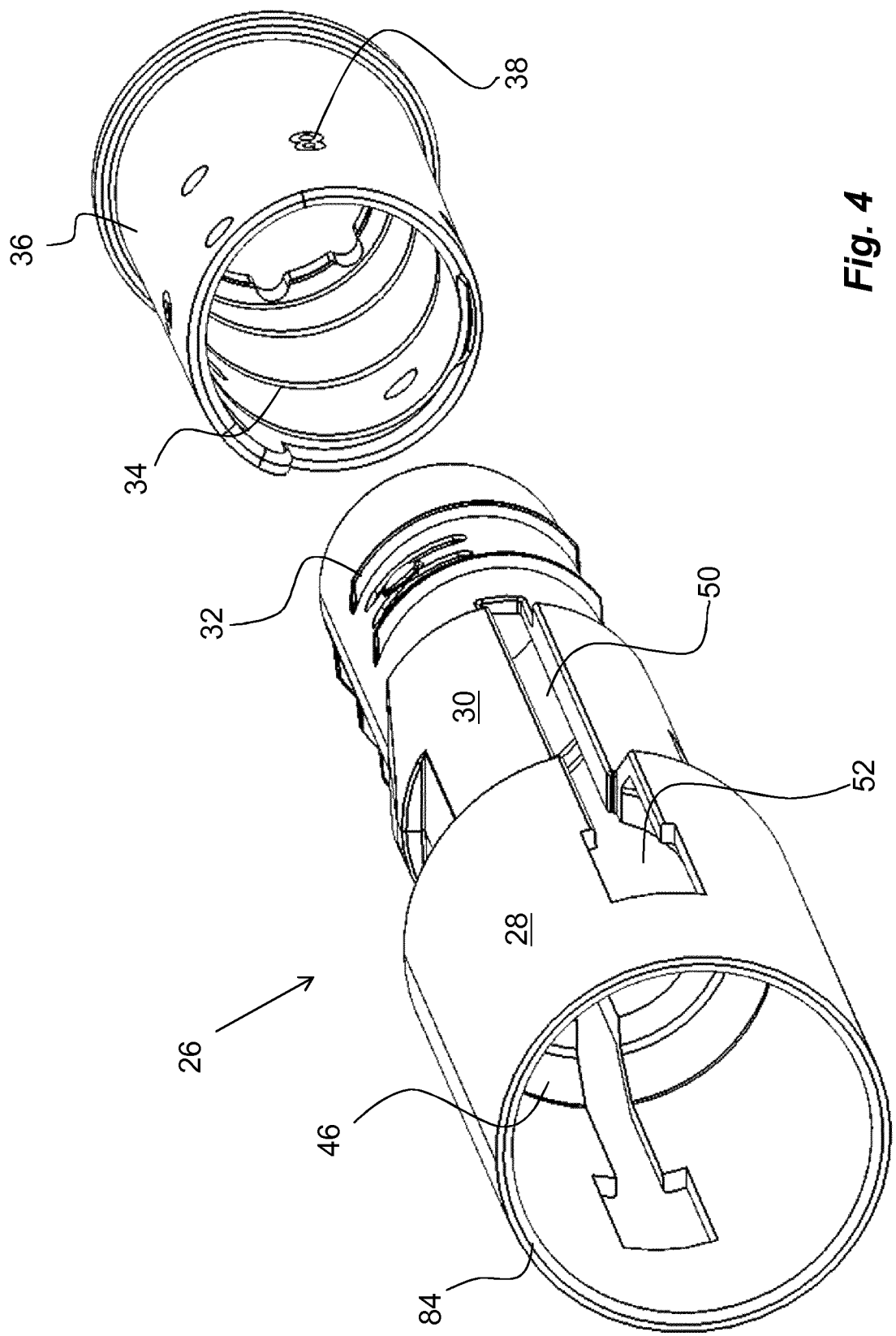

Surrounding the medicament container holder 24 and coaxial therewith is a medicament delivery member shield 26, FIGS. 3 and 4. The medicament delivery member shield 26 is arranged with a distal tubular part 28, which transforms into a proximal tubular part 30, FIG. 4. In this respect, the inner diameter of the proximal tubular part 30 is somewhat larger than the outer diameter of the medicament container holder 24. Further, the outer diameter of the proximal tubular part 30 is somewhat smaller than the second tubular part 16b of the proximal housing part 16 such that the medicament delivery member shield 26 can move in the longitudinal direction in relation to the proximal housing part 16.

An outer surface of the medicament delivery member shield 26 is arranged with threads 32, FIG. 4, which threads 32 are arranged to cooperate with corresponding threads 34, FIG. 4, on an inner surface of a generally tubular element 36, hereafter named depth adjuster. The outer surface of the depth adjuster 36 is arranged with indicia 38, such as numbers. These indicia 38 are to cooperate with a cut-out 40, FIG. 3, in the proximal end of the second tubular part 16b.

The medicament container holder 24 is further arranged with a circumferential outwardly extending ledge 42 at its distal area, FIG. 3. A medicament delivery member return force element 44, in the embodiment shown arranged as a compression spring, is arranged between a proximally directed surface of the ledge 42 and a distally directed circumferential ledge 46 of the medicament delivery member shield 26, FIG. 4, wherein the medicament delivery member return force element 44 urges the medicament container holder 24 and the medicament container 18 in the distal direction. The medicament container holder 24 is also arranged with a longitudinal, outwardly directed ledge 48 on its outer surface, FIG. 3, which ledge 48 is intended to fit into a longitudinally extending groove 50 in the medicament delivery member shield 26 for guide purposes. Further, the groove 50 ends in a somewhat larger cut-out 52, FIGS. 3 and 4, in the distal area of the distal tubular part 28 of the medicament delivery member shield, the function of which will be described below.

Figure 5:
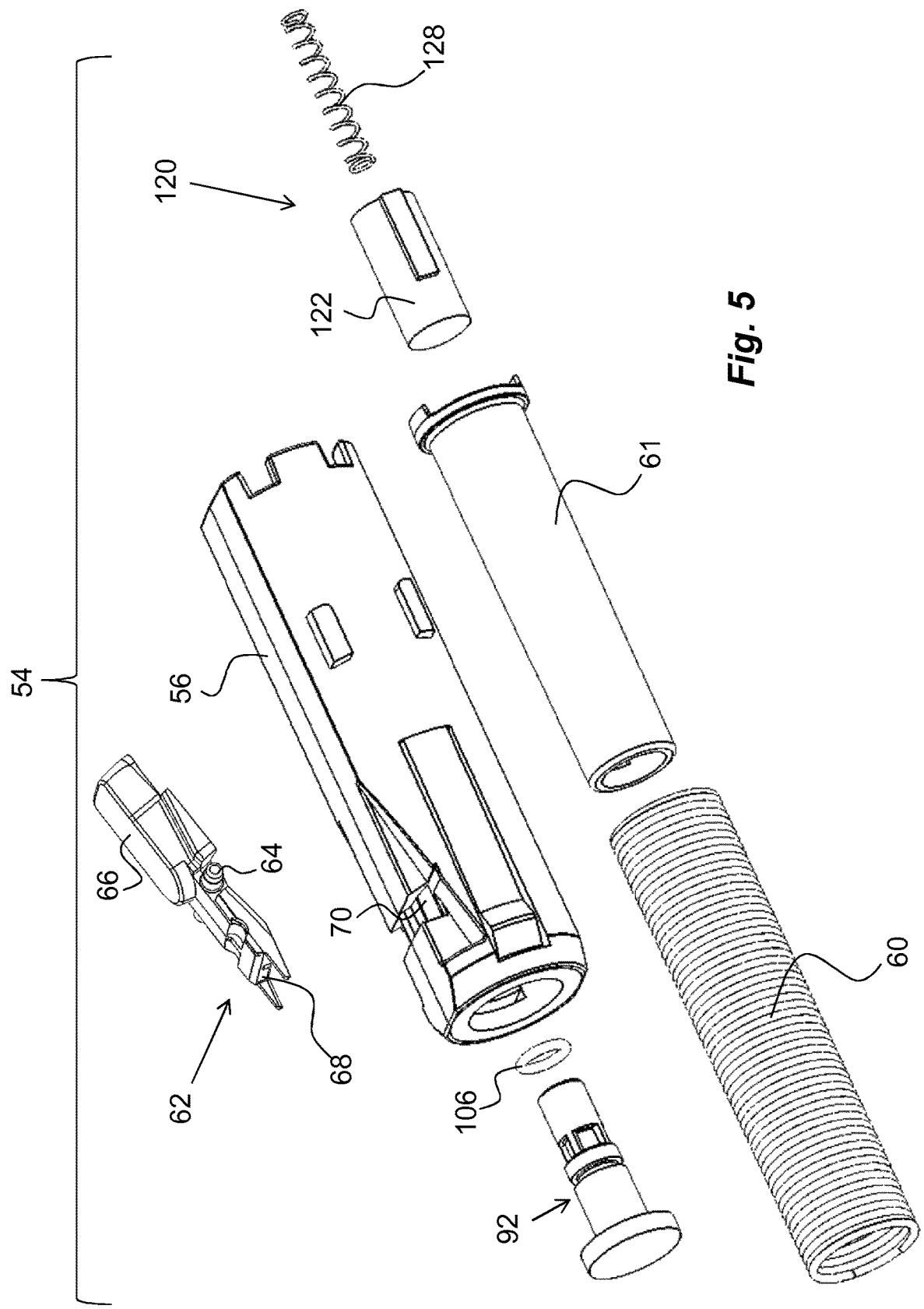

The device further comprises a drive mechanism 54, FIGS. 2 and 5. The drive mechanism 54 comprises a plunger rod driver 56 arranged axially moveable within the main housing 10 between a distal end position and a proximal end position. The proximal end of the plunger rod driver 56 is operably connected to a distal end of an elongated plunger rod 58, FIG. 2, which in turn abuts the movable stopper 22 in the medicament container 18. The proximal end position of the plunger rod driver 56 corresponds to a position where the plunger rod 58 and the stopper 22 have been pressed to the end of the stroke of the plunger rod 58, i.e. the medicament container 18 has been emptied, and the distal end position of the plunger rod driver 56 corresponds to a position where the plunger rod 58 and the stopper 22 have not yet been moved, i.e. the medicament container 18 is full.

Figure 6:
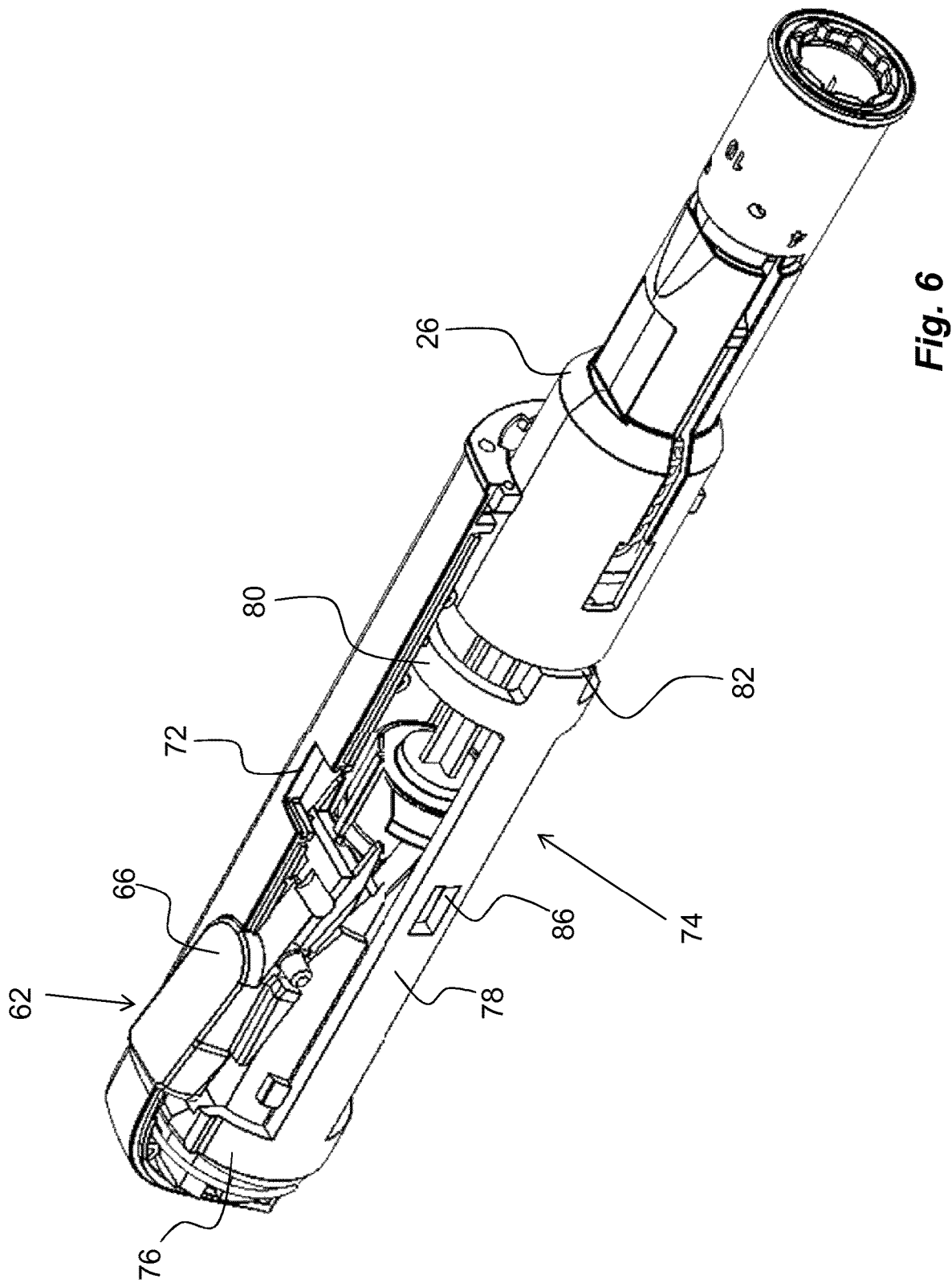

The drive mechanism 54 further comprises a drive spring 60, shown in the form of a helical coil spring, FIG. 5, which biases the plunger rod driver 56 towards its proximal end position. The drive spring 60 is supported by a tubular support element 61 that will prevent buckling of the drive spring 60. A manually operated release mechanism 62, FIGS. 4 and 5, for releasing the plunger rod driver 56 of the drive mechanism 54 from the distal, or cocked, position to the proximal, or extended, position is arranged at an outer surface of the housing 10. The release mechanism 62 is pivotable around a pivoting axle 64, FIG. 5, between an extended position and a depressed position and comprises a trigger button 66, which is operably connected to a drive mechanism locking element 68 which locks and interacts with the plunger rod driver 56 via a proximally directed ledge 70 to hold the plunger rod driver 56 with the drive spring 60 in the tensioned state. Adjacent, or at least near, the release mechanism 62, a status window 72, FIG. 6, is arranged through which symbols provided on the plunger rod driver 56 are visible to indicate the status of the medicament delivery device. The status window 72 is preferably made of a transparent, or at least translucent, plastic material.

Further, a blocking mechanism 74, FIG. 6, is arranged to operatively act on the release mechanism 62 for preventing actuation of the release mechanism 62 in a first position and to allow actuation of the release mechanism 62 in a second position. The blocking mechanism 74 comprises a generally ring-shaped blocking element 76 surrounding the plunger rod driver 56 and is in an initial position positioned distally of the release mechanism 62 such that a part of the blocking element 76 is radially inside the distal end of the trigger button 66, as shown in FIG. 6. In this position, the trigger button 66 is prevented from pivoting around the pivoting axle 64, thus preventing the activation of the device.

The ring-shaped blocking element 76 is arranged with two proximally directed arms 78, which arms 78 are interconnected by a proximal ring-shaped second element 80. The arms 78 end in proximally directed end surfaces 82, FIG. 6. The proximally directed end surfaces 82 are arranged to be in contact with a distally directed end surface 84, FIG. 4, of the needle shield 26, the function of which will be described below. The arms 78 are further arranged with cut-outs 86, FIG. 6, the function of which will be described below.

Figure 7:
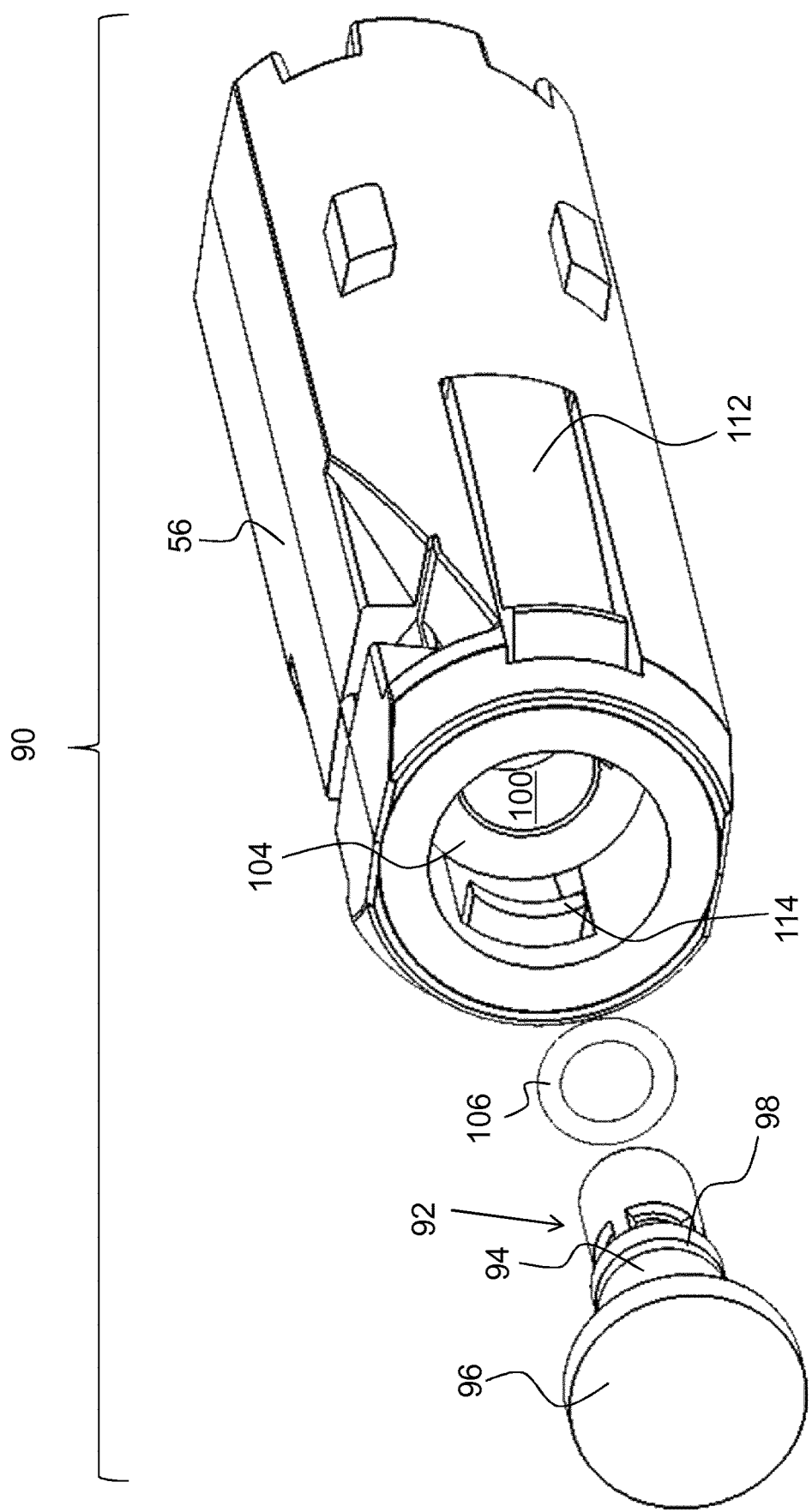

According to the embodiment, the device is arranged with a signal generating mechanism 90, FIG. 7. It comprises a signal generating element 92 comprising an elongated tubular body 94, provided with a circular end plate 96 with a proximally directed end surface, which is intended to be in contact with a distally directed end surface of the plunger rod 58. Further, the side surface of the body 94 of the signal generating element 92 is arranged with a circumferential groove 98, FIG. 7. The body 94 is arranged to fit into a central passage 100 of a tubular element 102 attached to a proximal area of the plunger rod driver, FIGS. 7 and 8. The tubular element 102 is arranged with a proximally directed annular surface 104 at the proximal end of the plunger rod driver 56, FIG. 7. The area of the plunger rod driver 56 proximal of the annular surface 104 has a diameter somewhat larger than the diameter of the end plate 96, such that the latter may fit into the proximal end of the plunger rod driver 56.

Figure 8:
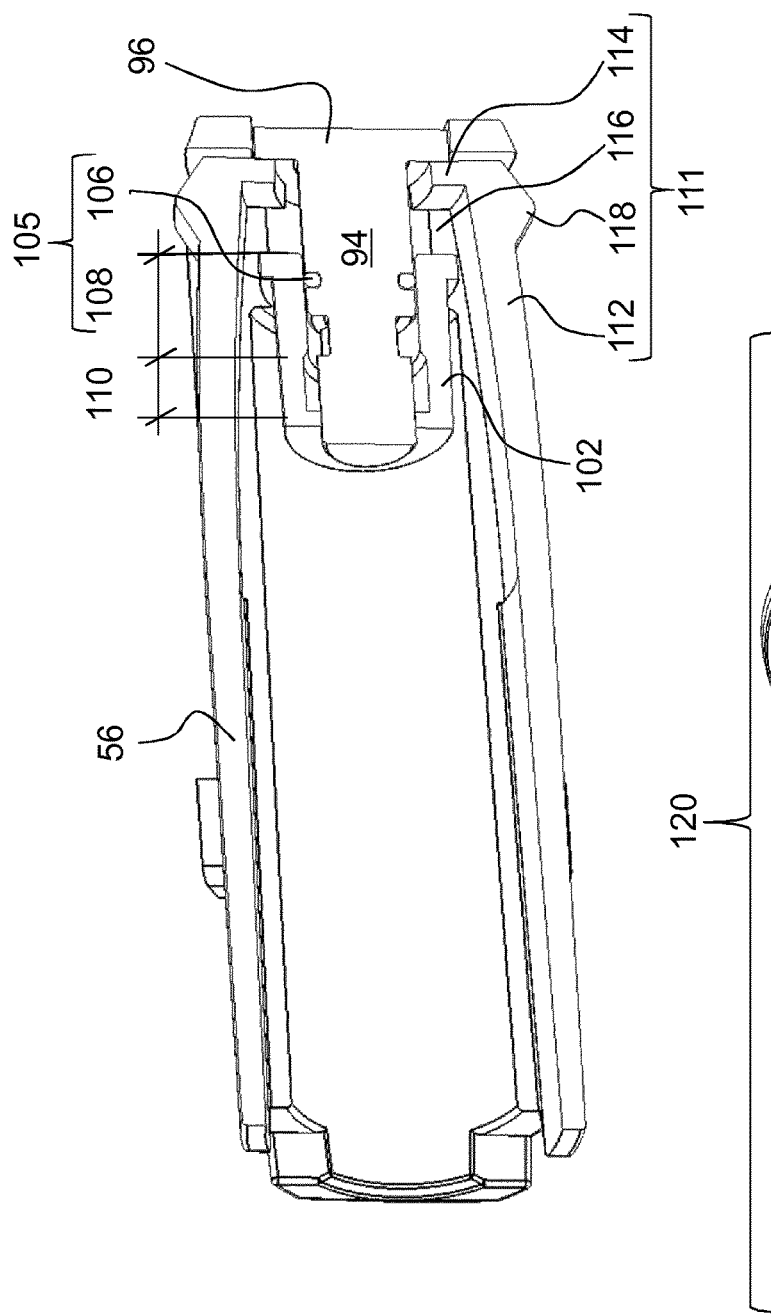

Further a signal delay mechanism 105 is arranged, FIG. 8. It comprises a friction enhancing element 106 intended to fit into the circumferential groove 98 of the signal generating element 92. In the embodiment shown the friction enhancing element is an O-ring made of a resilient material such as rubber. The central passage 100 of the tubular element 102 is arranged with a first section 108, FIG. 8, having a diameter somewhat smaller than the diameter of the O-ring when fitted into the circumferential groove such that the O-ring is compressed when placed in the first section 108, which first section is comprised in the signal delay mechanism 105. The central passage 100 is further arranged with a second section 110, FIG. 8, that has a diameter that is slightly larger than the diameter of the O-ring, the function of which will be described below.

Further, a signal release mechanism 111, FIG. 8, is provided on the plunger rod driver 56. It comprises two arms 112, FIGS. 7 and 8, attached to the plunger rod driver and extend in the proximal direction, where the arms 112 are positioned on opposite sides of the central passage 100. Each arm 112 is arranged with a generally radially inwardly directed ledge 114. The inwardly directed ledges 114 are arranged to extend into cut-outs 116 in the central passage 100. Further the arms 112 are arranged with generally radially outwardly extending ledges 118, the function of which will be described below.

Figure 9:
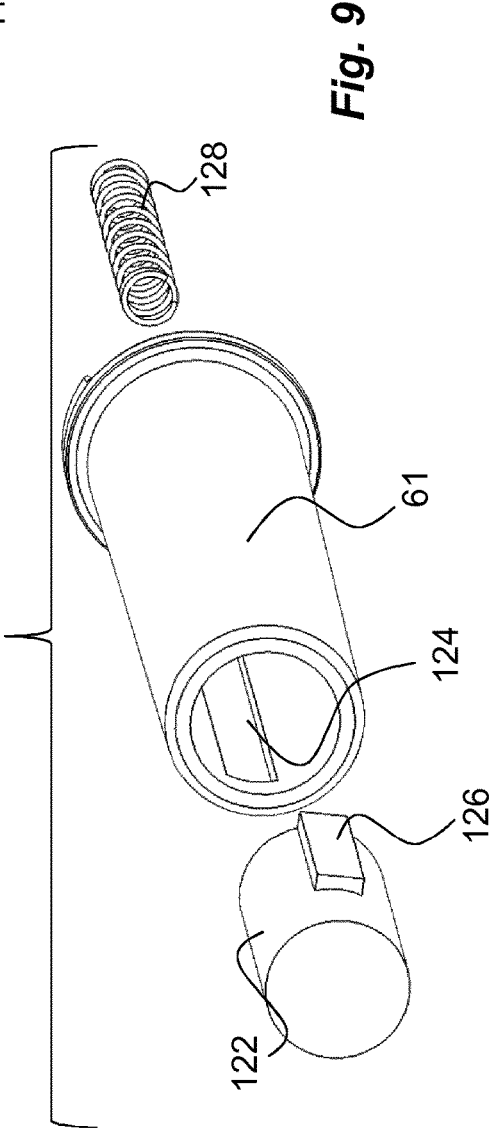
Figure 10:
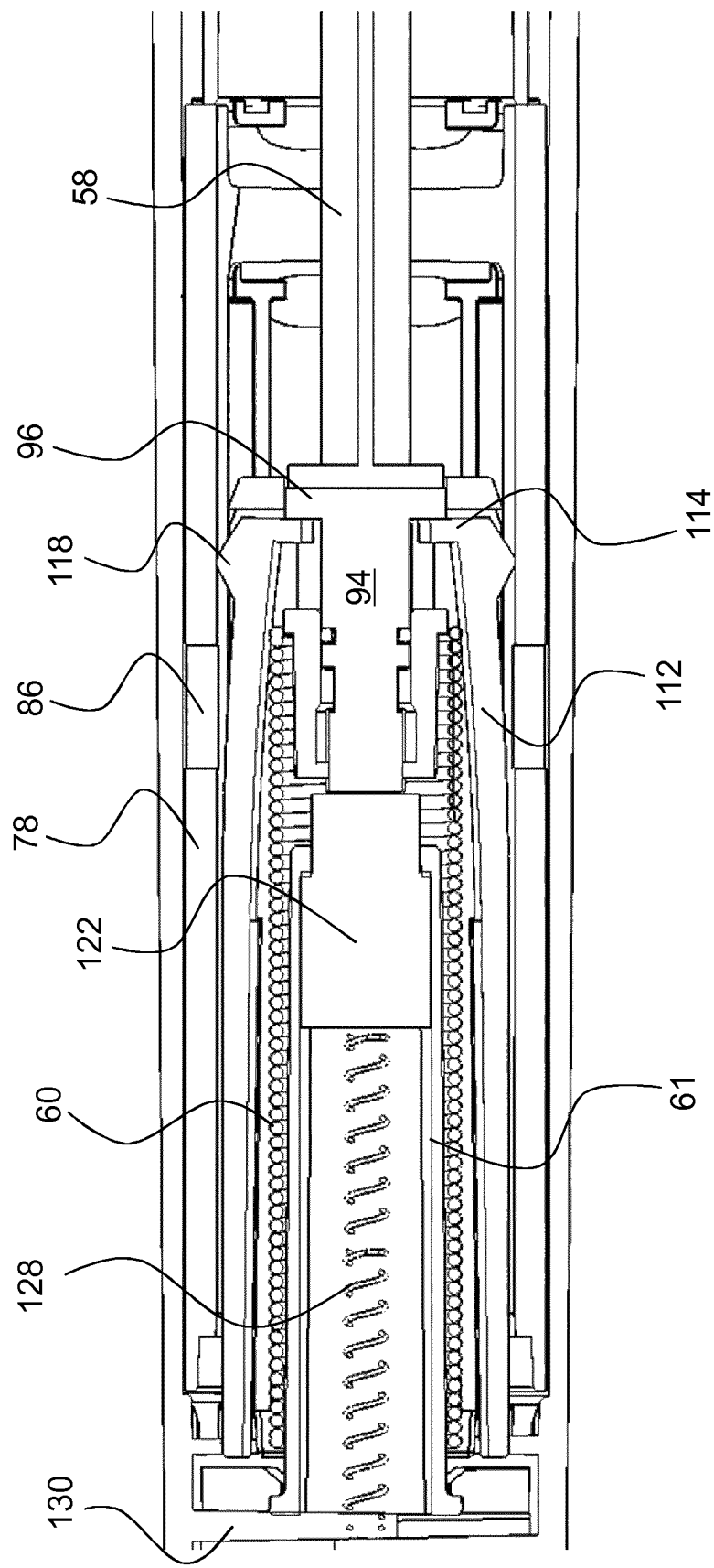

The device is further arranged with a signal element return mechanism 120, FIG. 9. It comprises a generally cylindrical pusher element 122 arranged slidable inside the support element 61. The support element 61 is arranged with longitudinally extending grooves 124 on its inner surface and the pusher element 122 is arranged with corresponding ledges 126 that fit into the grooves. The grooves end a certain distance before the proximal end of the support element 61 as seen in FIG. 9, whereby the end surface of the groove 124 will provide a stop surface for a proximally directed end surface of the ledges 126, thereby limiting the movement in the proximal direction of the pusher element 122 relative to the support element 61. The signal element return mechanism 120 is further provided with a compression spring 128 arranged to act on a distally directed end surface of the pusher element and a fixed wall 130 in the housing 10, as seen in FIG. 10.

The device is intended to function as follows. When the device is delivered to the user, the medicament delivery member shield 26 is in an extended, proximal position where the medicament delivery member 20 is shielded, FIG. 6. There is thus no risk for unintentional needle sticks. The plunger rod 58 is in a distal position where the plunger rod driver 56 is locked in a loaded state with the drive spring 60 compressed as seen in FIG. 10. The user then turns the depth adjuster 36 to set the desired or required penetration depth, which is displayed by the indicia 38.

The device is now ready to use and the user presses a proximal end of the medicament delivery member shield 26 against a dose delivery site, whereby the medicament delivery member shield 26 is moved in the distal direction inside the housing of the device. Upon pressing the device against the injection site, the medicament delivery member shield 26 also comes into contact with the proximally directed end surfaces 82 of the arms 78 of the blocking mechanism 74. Thus the ring-shaped blocking element 76 of the blocking mechanism 74 is moved out of blocking position, allowing the release mechanism 62 to be activated. The next step is then for the user to activate the dose delivery sequence.

According to the embodiment shown, the user depresses the trigger button 66 of the release mechanism 62, whereby the drive spring 60 is released in that the drive mechanism locking element 68 is moved out of contact with the plunger rod driver 56. The plunger rod driver 56 and the drive spring 60 then act to force the plunger rod 58 in the proximal direction acting on the stopper 22 inside the medicament container 18. Since the medicament is incompressible and the passage through the medicament delivery member 20 is narrow, the medicament container holder 24 with the medicament container 18 will be moved in the proximal direction, against the comparatively weak force of the medicament delivery member return force element 44.

The movement of the medicament container 18 will now cause a penetration of the medicament delivery member 20 into the skin of the user. The force of the drive spring 60 is far more powerful than that of the medicament delivery member return force element 44, which therefore is compressed when the drive mechanism 54 is released. The penetration movement is stopped when the circumferential ledge 42 of the distal end of the medicament container holder is adjacent a distally directed stop ledge (not shown) of the medicament delivery member shield 26 with the fully compressed medicament delivery member return force element 44 between the ledges.

The force of the drive spring 60 now forces the plunger rod 58 in the proximal direction in relation to the medicament container 18, moving the stopper 22 in the proximal direction, whereby a dose of medicament is delivered into the body of the user. When the plunger rod 58 is moving in the proximal direction, so is the signal generating element 92. This is due to the arms 112 being forced radially inwards due to the outwardly directed ledges 118 being in contact with an inner surface of the arms 78 of the blocking mechanism 74 as seen in FIG. 10. The inwardly directed ledges 114 of the arms 112 are then abutting a distally directed surface, abutment surface, of the end plate 96 of the signal generating element 92.

When the plunger rod driver 56, the signal generating element 92, the plunger rod 58 and the stopper 22 have reached a position close to the proximal end position of the stopper 22, the outwardly directed ledges 118 will enter the cut-outs 52 of the medicament delivery member shield 26, as seen in FIG. 11. The arms 112 are then free to move radially outwardly when the outwardly directed ledges enter the cut-outs 52. Thereby, the inwardly directed ledges 114 will be moved out of contact with the end plate 96 of the signal generating element 92, as seen in FIG. 12.

The force of the drive spring 60 will continue to urge the plunger rod driver 56 in the proximal direction causing it to move in relation to the signal generating element 92. However, the relative movement between the plunger rod driver 56 and the signal generating element 92 is slowed due to the friction enhancing element 106 frictionally acting on the inner surface of the tubular element 102 of the plunger rod driver 56. The friction also aids in transferring some force to the plunger rod 58, ending the injection sequence.

Figure 13:
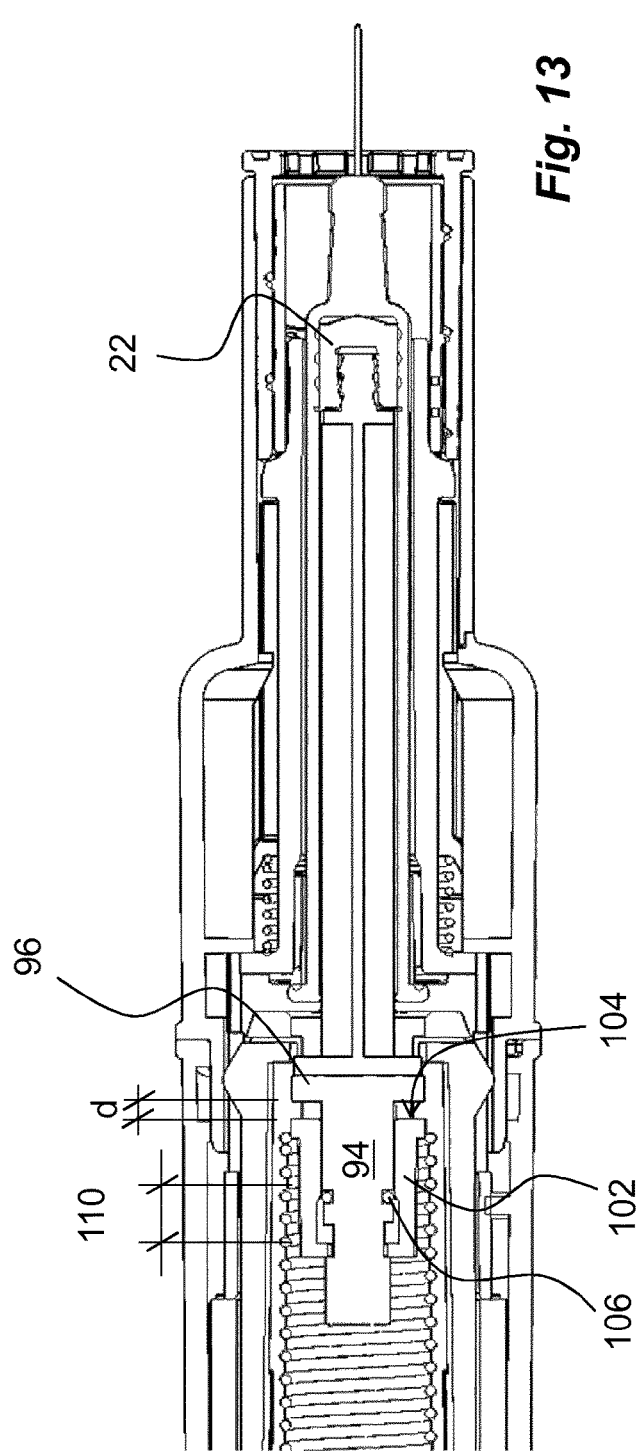
Figure 14:
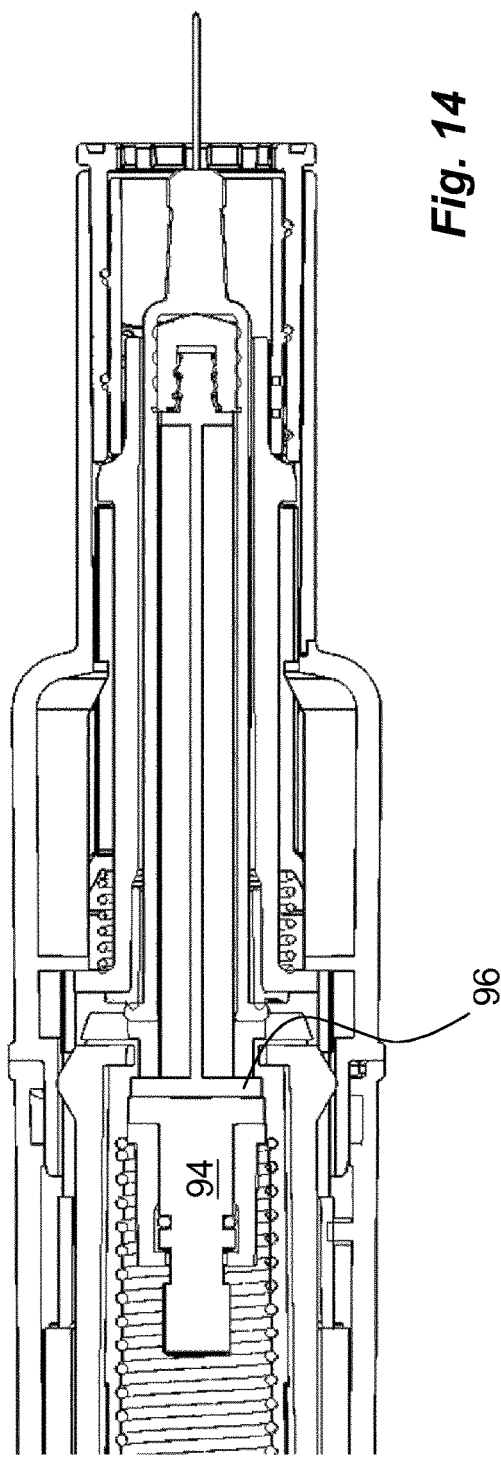

The relative movement continues between the plunger rod driver 56 and the signal element 92. When the friction enhancing element 106 has been moved along the first section 108 it reaches the second section 110, as seen in FIG. 13. Now the friction enhancing element 106 is moved out of contact with the inner surface of the tubular element 102. As seen, the distally directed surface of the end plate, the abutment surface, is positioned a distance d from the annular surface 104, an abutment surface. The spring force still acts on the plunger rod driver 56 and since it now can move freely, it will accelerate in the proximal direction the distance d until the proximal annular surface 104, the abutment surface, of the plunger rod driver 56 hits the distally directed surface, the abutment surface, of the end plate 96 of the signal generating element 92, as seen in FIG. 14. The impact will cause an audible as well as a tactile signal, indicating to the user that the injection sequence has ended and that it is safe to remove the medicament delivery device. In this respect it is to be understood that the length of the first section may be varied in order to vary the delay time before signalling. It is also possible to alter the actuation point by making the cut-outs 52 longer or shorter or to position them differently with respect to the plunger rod driver 56 and its positions during injection.

When removing the device, since the force on the medicament delivery member shield 26 now is removed at its proximal end, the medicament delivery member return force element 44 will force the medicament delivery member shield 26 in the proximal direction, whereby the medicament delivery member 20 is again shielded by the medicament delivery member shield 26. In its extended position, the medicament delivery member shield 26 is locked by a medicament delivery member shield locking mechanism (not shown).

When the device is to be used again, the proximal housing part 16 is removed from the main housing part 10. This may be done by turning the housing parts in relation to each other, if for instance a bayonet connection is used.

In order to reset the device the plunger rod driver 56 has to be moved back to its initial position. This may be done by pushing on the plunger rod driver 56 in the distal direction with a suitable tool. This will cause the drive spring 60 to be again tensioned until the drive mechanism locking element 68 grips and holds the plunger rod driver 56. Before resetting, the signal generating element 92 is still in the distal position and the arms 112 are in their outwardly flexing position, as seen in FIG. 15. When the plunger rod driver 56 now is moved back in the distal direction, the outwardly extending ledges 118 will come in contact with the arms 78 of the release mechanism blocking mechanism 74, and be forced radially inwards, as seen in FIG. 16. Since the signal generating element 92 is still in the distal position, the inwardly directed ledges 114 of the arms will be positioned proximally of the end plate 96, as seen in FIG. 16.

The plunger rod driver 56 continues to be moved distally until the distal end surface of the signal generating element 92 is moved into contact with the pusher element 122 of the signal element return mechanism 120, FIG. 17. The pusher element 122 is urged in the proximal direction by the spring 128, which will cause the signal generating element 92 to be moved proximally relative to the plunger rod driver 56 and its tubular element 102 as the latter continues in the distal direction. At a certain position, the outwardly directed ledges 118 will come in position with the cut-outs 86 whereby the arms 112 flex radially outwards, as seen in FIG. 18. This enables the end plate 96 of the signal generating element 92 to pass the inwardly directed ledges 114 of the arms 112 and to return to its initial position, FIG. 19, thereby resetting the signal mechanism.

The pushing of the plunger rod driver 56 in the distal direction can now be ended. The plunger rod driver 56 will now slide in the proximal direction by the force of the compression spring 60 until the drive mechanism locking element 68 grips into the ledge 70 of the plunger rod driver. The proximal movement of the plunger rod driver 56 causes the outwardly directed ledges 118 of the arms 112 to be moved out of the cut-outs 86, and again causes the arms 108 to be pushed radially inwards, thereby positioning the inwardly directed ledges 114 on the distal side of the end plate 96 of the signal element, FIG. 20. The device is now ready to be used for a subsequent injection.

It is to be understood that the embodiment described above and shown in the drawings is to be regarded only as a non-limiting example of the invention and that it may be modified in many ways within the scope of the patent claims.

The invention claimed is:

1. A medicament delivery device comprising:
   a housing having a distal end and a proximal end, said housing being adapted to receive a medicament container with a delivery member for delivery of a medicament;
   a drive mechanism arranged to act on a plunger rod, wherein the plunger rod is arranged to act on the medicament container for providing automatic delivery of the medicament;
   a release mechanism interactively connected to the drive mechanism for releasing the drive mechanism from a pre-tensioned state; and
   a signal generating mechanism for generating a signal indicating that the medicament has been completely delivered from the medicament container, wherein the signal generating mechanism is operably connected to said drive mechanism such that it is movably arranged in a longitudinal direction in relation to said drive mechanism,
   wherein the signal is at least one of audible, tactile and visual,
   wherein said drive mechanism is arranged with a signal release mechanism capable of activating said signal generating mechanism at a certain longitudinal position of said drive mechanism after release of the drive mechanism,
   wherein said signal generating mechanism comprises a signal delay mechanism operably arranged to delay the generation of the signal after activation of said signal generating mechanism,
   wherein the signal generating mechanism comprises a signal generating element that is arranged with a tubular body, and
   wherein said signal delay mechanism comprises a friction enhancing element that surrounds the tubular body of the signal generating element.

2. The medicament delivery device according to claim 1, wherein the friction enhancing element is arranged to act between said signal generating element and said drive mechanism.

3. The medicament delivery device according to claim 1, wherein the tubular body of the signal generating element is slidably arranged in a correspondingly shaped passage of said drive mechanism.

4. The medicament delivery device according to claim 3, wherein said friction enhancing element is arranged to frictionally act between the tubular body and a wall of said correspondingly shaped passage of said drive mechanism.

5. The medicament delivery device according to claim 3, wherein said correspondingly shaped passage of said drive mechanism comprises a first section having a first diameter such that said friction enhancing element is in contact with the first section.

6. The medicament delivery device according to claim 5, wherein said correspondingly shaped passage of said drive mechanism comprises a second section having a second diameter such that the friction enhancing element is not in contact with the second section.

7. The medicament delivery device according to claim 6, wherein said signal generating element comprises an abutment surface,
said abutment surface operably arranged to interact with a corresponding abutment surface on said drive mechanism for creating the signal when said abutment surfaces are moved in contact with each other.

8. The medicament delivery device according to claim 7, wherein said abutment surface is operably arranged to interact with said corresponding abutment surface on said drive mechanism for creating the signal when said abutment surfaces are moved in contact with each other, and wherein the signal is audible.

9. The medicament delivery device according to claim 7, wherein said abutment surface is operably arranged to interact with said corresponding abutment surface on said drive mechanism for creating the signal when said abutment surfaces are moved in contact with each other, and wherein the signal is tactile.

10. The medicament delivery device according to claim 7, wherein said abutment surfaces are positioned with a distance between each other when said friction enhancing element is moved from said first section to said second section.

11. The medicament delivery device according to claim 1, wherein said signal release mechanism comprises arms flexible in a radial direction between a holding position and a release position.

12. The medicament delivery device according to claim 11, wherein said arms are held in the holding position by a support surface positioned radially outside said arms.

13. The medicament delivery device according to claim 12, wherein said support surface positioned radially outside said arms terminates at said certain longitudinal position of said drive mechanism.

14. The medicament delivery device according to claim 12, further comprising a signal element return mechanism operably connected to said signal generating mechanism for returning the signal generating element of the signal generating mechanism to an initial position of the signal generating element.

15. The medicament delivery device according to claim 14 wherein the signal element return mechanism is operably connected to said signal generating mechanism for returning said signal generating element to the initial position of the signal generating element when said drive mechanism is returned to an initial position of the drive mechanism.

16. The medicament delivery device according to claim 14, wherein said signal element return mechanism comprises a pusher element capable of contacting said signal element causing a relative movement between said signal generating element and said drive mechanism.

17. The medicament delivery device according to claim 14, wherein said support surface is arranged such as to act on said arms for holding said signal generating element after it has been brought to the initial position of the signal generating element by said signal element return mechanism.

18. The medicament delivery device according to claim 1, wherein said friction enhancing element is made of a resilient material.

19. The medicament delivery device according to claim 1, wherein said friction enhancing element comprises rubber.

20. The medicament delivery device according to claim 1, wherein said friction enhancing element comprises plastic.

21. The medicament delivery device according to claim 1, wherein said friction enhancing element comprises an O-ring, and
wherein said signal generating element is arranged with a groove in which said O-ring fits.

* * * * *